United States Patent
Venugopala et al.

(10) Patent No.: US 11,945,819 B1
(45) Date of Patent: Apr. 2, 2024

(54) DIMETHYL 7-BROMO-1-(4-SUBSTITUTED BENZOYL)PYRROLO[1,2-A]QUINOLINE-2,3-DICARBOXYLATES AS ANTI-INFLAMMATORY AGENTS

(71) Applicant: KING FAISAL UNIVERSITY, Al-Ahsa (SA)

(72) Inventors: Katharigatta N. Venugopala, Al-Ahsa (SA); Pran Kishore Deb, Al-Ahsa (SA); Pramod Patil, Al-Ahsa (SA); Osama I. Alwassil, Al-Ahsa (SA); Mohamed A. Morsy, Al-Ahsa (SA); Bandar Aldhubiab, Al-Ahsa (SA); Vijaykumar Uppar, Al-Ahsa (SA); Mahmoud Kandeel, Al-Ahsa (SA); Praveen B. Managutti, Al-Ahsa (SA); Basavaraj Padmashali, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/371,126

(22) Filed: Sep. 21, 2023

(51) Int. Cl.
*A61K 31/4353* (2006.01)
*A61P 29/00* (2006.01)
*C07D 471/04* (2006.01)
*C07D 471/16* (2006.01)

(52) U.S. Cl.
CPC ............ *C07D 471/04* (2013.01); *A61P 29/00* (2018.01); *C07B 2200/13* (2013.01)

(58) Field of Classification Search
CPC .......................... A61K 31/4353; C07D 471/16
USPC ............................................. 514/294; 546/94
See application file for complete search history.

(56) References Cited

FOREIGN PATENT DOCUMENTS

IN 201941039384 A 3/2020

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Uppar, Vijayakumar, et al. "Investigation of antifungal properties of synthetic dimethyl-4-bromo-1-(substituted benzoyl) pyrrolo [1, 2-a] quinoline-2, 3-dicarboxylates analogues: Molecular docking studies and conceptual DFT-based chemical reactivity descriptors and pharmacokinetics evaluation." Molecules 26.9 (2021): 2722.
Gomha, Sobhi M., and Kamal M. Dawood. "Synthesis of novel indolizine, pyrrolo [1, 2-a] quinoline, and 4, 5-dihydrothiophene derivatives via nitrogen ylides and their antimicrobial evaluation." Journal of Chemical Research 38.9(2014): 515-519.
Uppar, Vijayakumar, et al. "Microwave induced synthesis, and pharmacological properties of novel 1-benzoyl-4-bromopyrrolo [1, 2-a] quinoline-3-carboxylate analogues." Chemical Data Collections 25 (2020): 100316.
Venugopala, Katharigatta N., et al. "Cytotoxicity and antimycobacterial properties of pyrrolo [1, 2-a] quinoline derivatives: Molecular target identification and molecular docking studies." Antibiotics 9.5 (2020): 233.
Uppar, Vijayakumar, et al. "Synthesis and characterization of pyrrolo [1, 2-a] quinoline derivatives for their larvicidal activity against Anopheles arabiensis." Structural Chemistry 31 (2020): 1533-1543.
Khalifa, Nagy M., et al. "Anti-inflammatory and analgesic activities of some novel carboxamides derived from 2-phenyl quinoline candidates." Biomed. Res 28.2 (2017): 869-874.
Dawood, Kamal M., Eman A. Ragab, and Sanaa N. Mohamed. "Synthesis of Some New Indolizine and Pyrrolo [1, 2-a] quinoline Derivatives via Nitrogen Ylides." Zeitschrift für Naturforschung B 64.4 (2009): 434-438.

* cited by examiner

*Primary Examiner* — Douglas M Willis
(74) *Attorney, Agent, or Firm* — Nath, Goldberg & Meyer; Richard C. Litman

(57) ABSTRACT

Novel dimethyl 7-bromo-1-(4-substituted benzoyl)pyrrolo[1,2-α]quinoline-2,3-dicarboxylates compounds, having the structure:

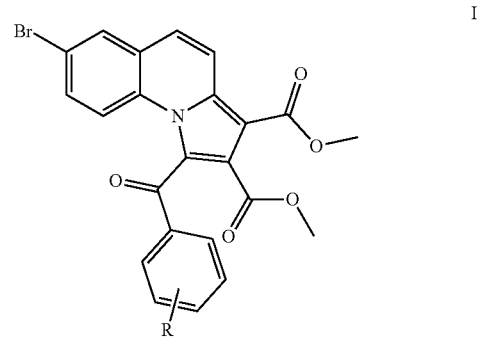

A method of synthesizing said compounds, a pharmaceutical composition comprising said compounds and a suitable carrier, and a method of using the compounds. The dimethyl 7-bromo-1-(4-substituted benzoyl)pyrrolo[1,2-α]quinoline-2,3-dicarboxylates compounds, identified as anti-inflammatory agents, are useful for treating inflammation, pain, and swelling in a patient.

17 Claims, No Drawings

DIMETHYL 7-BROMO-1-(4-SUBSTITUTED BENZOYL)PYRROLO[1,2-A]QUINOLINE-2,3-DICARBOXYLATES AS ANTI-INFLAMMATORY AGENTS

BACKGROUND

1. FIELD

The present disclosure provides novel dimethyl 7-bromo-1-(4-substituted benzoyl)pyrrolo[1,2-α]quinoline-2,3-dicarboxylates compounds that exhibit anti-inflammatory activity, compositions containing such compounds and method of preparation. These compounds and compositions are useful as therapeutic agents for treating inflammation.

2. DESCRIPTION OF THE RELATED ART

Non-steroidal anti-inflammatory drugs (NSAIDs) have been therapeutically used in the medication of rheumatic arthritis and also in the treatment of various inflammatory disorders. Due to their gastrointestinal side effects, such NSAIDs are often used in limited numbers.

Thus, there exists a need to develop novel anti-inflammatory agents which may not cause gastrointestinal side effects.

SUMMARY

The present subject matter relates to the use of novel dimethyl 7-bromo-1-(4-substituted benzoyl)pyrrolo[1,2-α]quinoline-2,3-dicarboxylates with improved potential for treating inflammation, pain, and swelling.

In this regard, a series of dimethyl 7-bromo-1-(4- substituted benzoyl)pyrrolo[1,2-α]quinoline-2,3-dicarboxylates has been achieved by a synthetic method and purified by recrystallization and column chromatographic methods. The compounds may be obtained in good yields. Structural elucidation of the compounds may be completed by spectral techniques such as FT-IR, $^1$H-NMR, and $^{13}$C-NMR. These compounds were evaluated for their anti-inflammatory activity and show promising anti-inflammatory activity between millimolars to micromolar concentrations compared to standard anti-inflammatory drugs. Some of the selected lead compounds may be successfully taken forward to develop novel anti-inflammatory drug candidates.

Accordingly, the present subject matter provides novel 7-bromo-1-(4-substituted benzoyl)pyrrolo[1,2-α]quinoline-2,3-dicarboxylates compounds, for example, 7-bromo-1-(4-substituted benzoyl)pyrrolo[1,2-α]quinoline-2,3-dicarboxylates compounds of the general formula/structure I, as useful anti-inflammatory agents. The present subject matter further provides a process for the synthesis of such compounds, pharmaceutical compositions containing these compounds, and their use in therapy for the treatment of inflammation in a patient, either alone or in combination with other active ingredients.

In an embodiment, the present subject matter relates to a compound having the formula I:

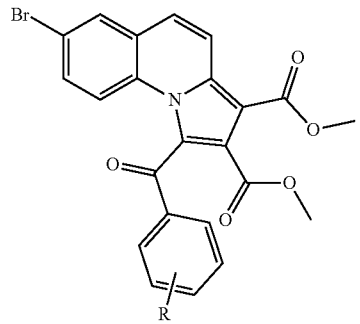

or a pharmaceutically acceptable salt, ester, stereoisomer, or solvate thereof, wherein:
R is a halogen.

In another embodiment, the present subject matter relates to a compound having the formula I:

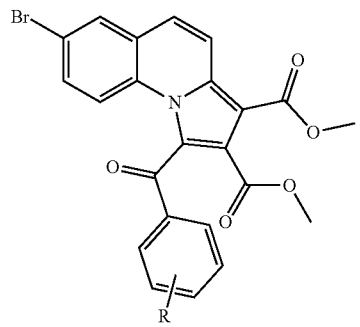

or a pharmaceutically acceptable salt, ester, stereoisomer, or solvate thereof, wherein:
R is a halogen selected from the group consisting of fluorine, bromine, and chlorine.

In an embodiment, the present subject matter relates to a compound selected from the group consisting of: dimethyl 7-bromo-1-(4-fluorobenzoyl)pyrrolo[1,2-α]quinoline-2,3-dicarboxylate (3a), dimethyl 7-bromo-1-(4-chlorobenzoyl)pyrrolo[1,2-α]quinoline-2,3-dicarboxylate (3b), dimethyl 7-bromo-1-(4-bromobenzoyl)pyrrolo[1,2-α]quinoline-2,3-dicarboxylate (3c), and a pharmaceutically acceptable salt, ester, stereoisomer, or solvate thereof.

In an embodiment, the present subject matter relates to a process for the synthesis of the compounds of formula I, including a number of species or specific structures falling under structural formula I. Further contemplated herein are pharmaceutical compositions containing these compounds, as well as methods of inhibiting inflammation and treating pain and swelling in a patient by administering such compounds.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, iodo, and bromo.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable minor images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as inflammation.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the use of novel dimethyl 7-bromo-1-(4-substituted benzoyl)pyrrolo[1,2-α] quinoline-2,3-dicarboxylates with improved potential for treating inflammation, pain, and swelling.

In this regard, a series of dimethyl 7-bromo-1-(4-substituted benzoyl)pyrrolo[1,2-α]quinoline-2,3-dicarboxylates has been achieved by a synthetic method and purified by recrystallization and column chromatographic methods. The compounds may be obtained in good yields. Structural elucidation of the compounds may be completed by spectral techniques such as FT-IR, $^1$H-NMR, and $^{13}$C-NMR. These compounds were evaluated for their anti-inflammatory activity and show promising anti-inflammatory activity between millimolars to micromolar concentrations compared to standard anti-inflammatory drugs. Some of the selected lead compounds may be successfully taken forward to develop novel anti-inflammatory drug candidates.

Accordingly, the present subject matter provides novel 7-bromo-1-(4-substituted benzoyl)pyrrolo[1,2-α]quinoline-2,3-dicarboxylate s compounds, for example, 7-bromo-1-(4-substituted benzoyl)pyrrolo[1,2-α]quinoline-2,3-dicarboxylates compounds of the general formula/structure I, as useful anti-inflammatory agents. The present subject matter further provides a process for the synthesis of such compounds, pharmaceutical compositions containing these compounds, and their use in therapy for the treatment of inflammation in a patient, either alone or in combination with other active ingredients.

In an embodiment, the present subject matter relates to a compound having the formula I:

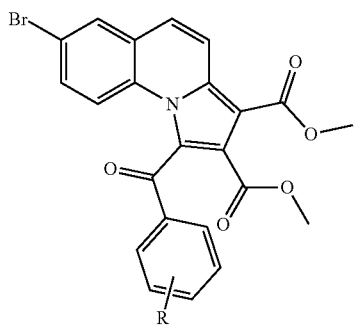

I or a pharmaceutically acceptable salt, ester, stereoisomer, or solvate thereof, wherein:

R is a halogen.

In a further embodiment, the present subject matter relates to compounds of formula I, wherein R is fluorine. In an embodiment in this regard, the compound can have a melting point between about 169 and about 171° C.

In still yet another embodiment, the present subject matter relates to compounds of formula I, wherein R is chlorine. In an embodiment in this regard, the compound can have a melting point between about 210 and about 212° C.

In another embodiment, the present subject matter relates to a compound of formula I, wherein R is bromine. In an embodiment in this regard, the compound can have a melting point between about 170 and about 172° C.

In an alternative embodiment, the present subject matter relates to compounds of formula I, wherein the compound is a crystal.

In one embodiment, the present subject matter relates to a compound of formula I, wherein the compound is capable of treating inflammation.

In another embodiment, the present subject matter relates to a compound having the formula I:

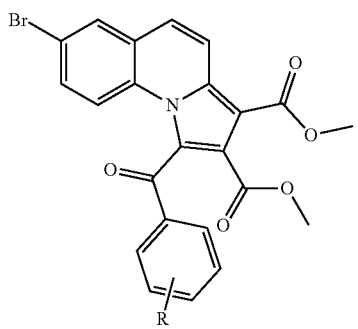

I or a pharmaceutically acceptable salt, ester, stereoisomer, or solvate thereof, wherein:

R is a halogen selected from the group consisting of fluorine, bromine, and chlorine.

In an embodiment, the present subject matter relates to a compound selected from the group consisting of: dimethyl 7-bromo-1-(4-fluorobenzoyl)pyrrolo[1,2-α]quinoline-2,3-dicarboxylate (3a), dimethyl 7-bromo-1-(4-chlorobenzoyl)pyrrolo[1,2-α]quinoline-2,3-dicarboxylate (3b), dimethyl 7-bromo-1-(4-bromobenzoyl)pyrrolo[1,2-α]quinoline-2,3-dicarboxylate (3c), and a pharmaceutically acceptable salt, ester, stereoisomer, or solvate thereof.

Said differently, the present subject matter can relate to compounds of formula I selected from the group consisting of:

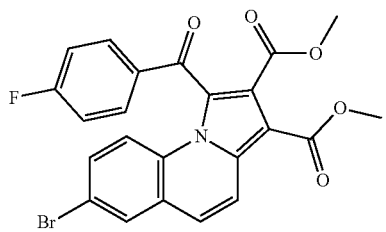

3a

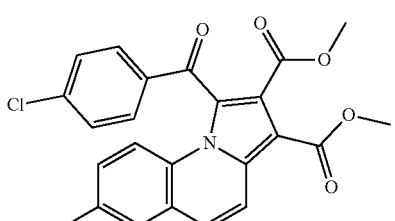

3b

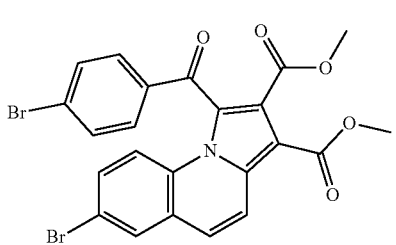

3c and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to the following general synthetic pathway. Specifically, synthesis commences with treating quaternary salts (1a-c) with dimethyl acetylene dicarboxylate (2) in the presence of $K_2CO_3$ in DMF solvent. The resulting mixture is stirred at room temperature for at least about 5 hours and the chemical reaction is monitored on TLC. The solid formed is separated by filtration, dried under a vacuum and recrystallized using ethanol to afford pyrrolo[1,2-α]quinoline derivatives (3a-c), as outlined in Scheme 1.

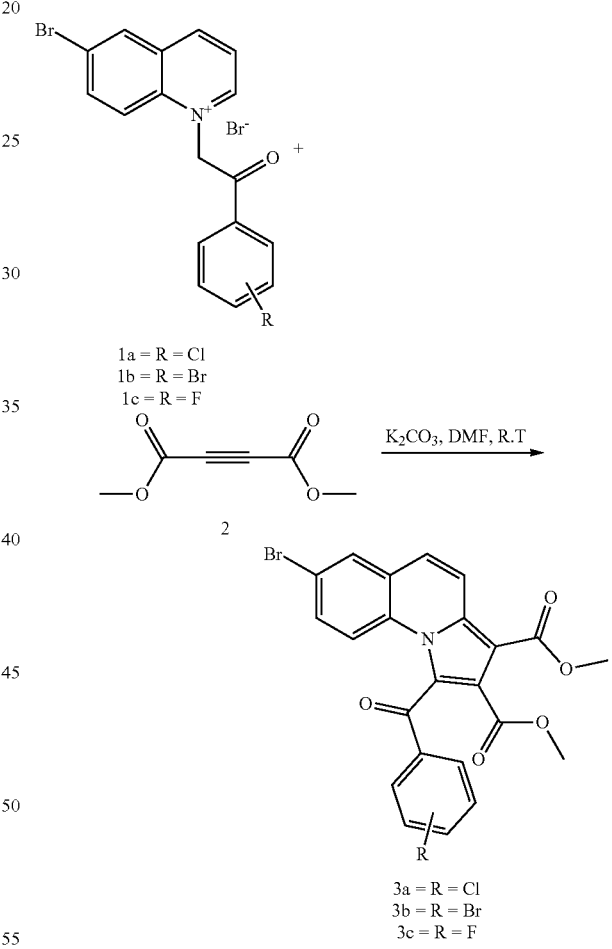

The newly synthesized compounds were characterized by FT-IR, $^1$H NMR, and $^{13}$C NMR.

In another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one or two of the present compounds, or one of the present compounds.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for inflammation, pain, and swelling. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of inflammation, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. Accordingly, the present subject matter further relates to use of the present compounds for the treatment of inflammation, pain, and swelling.

Accordingly, in an embodiment of the present subject matter, the dimethyl 7-bromo-1-(4- substituted benzoyl) pyrrolo[1,2-α]quinoline-2,3-dicarboxylates derivatives, or the dimethyl 7-bromo-1-(4-substituted benzoyl)pyrrolo[1,2-α]quinoline-2,3-dicarboxylates, as described herein were screened for their in vitro anti-inflammatory activity by inhibiting the bovine serum albumin denaturation method. The test compound is dissolved in a minimum amount of dimethyl sulphoxide (DMSO) and diluted with phosphate buffer. The final concentration of DMF in all solutions is less than 2.5%. Test solutions containing different concentrations of the drug is mixed with albumin solution in phosphate buffer and incubated at about 27-37° C.±10° C. for about at least 15 min. Denaturation is induced by keeping the reaction mixture at about 60° C.±10° C. in a water bath for at least about 10 min. After cooling, the turbidity is measured at about 210-660 nm (Shimadzu Spectrometer). Percentage inhibition of denaturation is calculated from a control where no drug was added. The percentage of inhibition is calculated from the following formula. The standard solution is also prepared as similar to that of the test solution. Ibuprofen can be used as a standard.

In an embodiment, the inhibition rate of Dimethyl 7-bromo-1-(4-fluorobenzoyl)pyrrolo[1,2-α]quinoline-2,3-dicarboxylate (3a) can be 49.75% at 10 µg.

In another embodiment, the inhibition rate of Dimethyl 7-bromo-1-(4-chlorobenzoyl)pyrrolo[1,2-α]quinoline-2,3-dicarboxylate (3b) can be 42.52% at 10 µg.

In a further embodiment, the inhibition rate of Dimethyl 7-bromo-1-(4-bromobenzoyl)pyrrolo[1,2-α]quinoline-2,3-dicarboxylate (3c) can be 54.35% at 10 µg.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used. Similarly, one or more of the present compounds can be used in combination therapy with one or more additional active agents.

The following examples relate to various methods of manufacturing certain specific compounds as described herein. All compound numbers expressed herein are with reference to the synthetic pathway figures shown above.

EXAMPLES

Example 1

Preparation of Dimethyl 7-bromo-1-(4-substituted benzoyl)pyrrolo[1,2-α]quinoline-2,3-dicarboxylates (3a-c)

Quaternary salts (1 mmol) were treated with dimethyl acetylene dicarboxylate (1 mmol) in the presence of $K_2CO_3$ in DMF solvent (10 mL). The resulting solution was stirred at room temperature for 5 h and the chemical reaction was monitored on TLC. The solid formed was separated by filtration, dried under a vacuum, and recrystallized using ethanol to afford pyrrolo[1,2-α]quinoline derivatives (3a-c). The newly synthesized compounds were characterized by FT-IR, $^1$H NMR, and $^{13}$C NMR. The structural details of the produced compounds are as follows.

Dimethyl 7-bromo-1-(4-fluorobenzoyl)pyrrolo[1,2-α] quinoline-2,3-dicarboxylate (3a) Brown color solid, m.p. 169-171° C.; FT-IR (KBr, cm$^{-1}$): ν 2995 (Ar—C—H), 1735 (Ester), 1703 (C═O), 1448 (Ar—C═C), 2948 (Alkane-C—H). $^1$H NMR (500 MHz, CDCl$_3$) δ=8.53 (s, 1H, Ar—H), 8.47 (s, 2H, Ar—H), 8.32 (d, 1H, Ar—H), 8.15 (s, 1H, aromatic), 7.55 (d, 1H, Ar—H), 7.53-7.38 (dd, 2H, ═CH Ar—H), 3.92 (s, OCH$_3$), 3.45 (s, OCH$_3$); $^{13}$CNMR (125.7 MHz, CDCl$_3$): 183.7 (C═O), 163.5 and 162.2 (2C═O of ester), 139.5, 138.7, 136.5(3C═C), 130.8, 129.5, 128.9, 126.5 125.4, 124.1, 118.9, 117.6 (Aromatic), 106.0 (=C—Br), 83.46, 77.03, 76.75 (3 =C—N), 52.7, 52.2 (2C—O), 30 (2 CH$_3$), 20.9 (6 C—F).

Dimethyl 7-bromo-1-(4-chlorobenzoyl)pyrrolo[1,2-α]quinoline-2,3-dicarboxylate (3b) Yellow color solid, m.p. 210-212° C.; FT-IR (KBr, cm$^{-1}$): v 3090 (Ar—C—H), 1734 (Ester), 1706 (C=O), 1480 (Ar—C=C), 2948 (Alkane-C—H). $^1$H NMR (500 MHz, CDCl$_3$) δ=8.31 (d, 1H, Ar—H), 7.95(s, 1H, Ar—H), 7.93(d, 1H, Ar—H), 7.55-7.49(dd, 2H, Ar—H), 7.55(s, 2H, Ar—H), 7.28(s, 2H, Ar—H), 3.94(s, 3H, —OCH$_3$), 3.51(s, 3H, —OCH$_3$); $^{13}$C NMR (125.7 MHz, CDCl$_3$): 186.32 (C=O), 164.91 and 163.52 (2C=O of ester), 140.70, 136.98, 135.85 (3C=C), 131.89, 131.41, 131.22, 129.14, 128.43, 126.92, 126.02, 120.57, 119.25 (Aromatic), 106.25 (=C—Br, =C—Cl), 77.33, 77.03, 76.80 (3 =C—N), 52.48, 51.95 (2C—O), 30 (2 CH$_3$).

Dimethyl 7-bromo-1-(4-bromobenzoyl)pyrrolo[1,2-α]quinoline-2,3-dicarboxylate (3c) Brown color Solid, m.p. 170-172° C.; FT-IR (KBr, cm$^{-1}$): v 2951 (Ar—C—H), 1734 (Ester), 1700 (C=O), 1447 (Ar—C=C), 2852 (Alkane-C—H), ESI-MS: m/z 545.95. $^1$H NMR (500 MHz, CDCl$_3$) δ: 8.31 (d, 2H, Ar—H), 7.85 (d, 2H, Ar—H), 7.68 (d, 1H, Ar—H), 7.28 (s, 1H, Ar—H), 3.93 (s, 3H, OCH$_3$), 3.51 (s, 3H, OCH$_3$); $^{13}$C NMR (125.7 MHz, CDCl$_3$): 186.45 (C=O), 164.86 and 163.36 (2C=O of ester), 137, 136.22, 132.13 (3C=C), 131.89, 131.38, 131.26, 129.46, 128.48, 126.90, 125.98, 120.53, 119.18 (Aromatic), 106.27 (=C—Br), 77.28, 77.03, 76.77 (3 =C—N), 52.48, 51.93 (2C—O), 30 (2 CH$_3$).

Pharmacological Activity

Example 2

In vitro Anti-inflammatory Activity

The newly synthesized compounds were screened for their in-vitro anti-inflammatory activity by inhibiting the bovine serum albumin denaturation method. The test compounds were dissolved in a minimum dimethyl sulphoxide (DMSO) and diluted with phosphate buffer (0.2M, pH 7.4). The final concentration of DMF in all solutions was less than 2.5%. Test solution (1 mL) containing different concentrations of the drug was mixed with 1 mL of 1 mm albumin solution in phosphate buffer and incubated at 27-37° C.±10° C. for 15 min. Denaturation was induced by keeping the reaction mixture at 60° C.±10° C. in a water bath for 10 min. After cooling, the turbidity was measured at 210-660 nm (Shimadzu Spectrometer). Percentage inhibition of denaturation was calculated from control where no drug was added. Each experiment was done in triplicate, and the average was taken. The percentage of inhibition is calculated from the following formula. The standard solution was also prepared as similar to that of the test solution. Ibuprofen was used as a standard.

The inhibition was calculated using the following equation:

% Inhibition=100 $(1-V_t/V_c)$ where, $V_t$=Drug absorbance of triplicate average $V_c$=Control absorbance of triplicate average In-vitro anti-inflammatory activity of dimethyl 7-bromo-1-(4-substituted benzoyl)pyrrolo[1,2-α]quinoline-2,3-dicarboxylates (3a-c) are illustrated in Table 1 below.

TABLE 1

| Compound code | % Inhibition at 10 μg |
|---|---|
| 3a | 49.75 |
| 3b | 42.52 |
| 3c | 54.35 |

It is to be understood that the dimethyl 7-bromo-1-(4-substituted benzoyl)pyrrolo[1,2-α]quinoline-2,3-dicarboxylates derivatives are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A compound having the formula I:

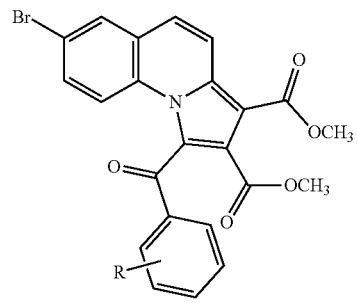

or a pharmaceutically acceptable salt thereof, wherein:

R is halogen.

2. The compound of claim 1, or a pharmaceutically acceptable salt thereof, wherein R is F.

3. The compound of claim 2, or a pharmaceutically acceptable salt thereof, wherein the compound has a melting point between 169° C. and 171° C.

4. The compound of claim 1, or a pharmaceutically acceptable salt thereof, wherein R is Cl.

5. The compound of claim 4, or a pharmaceutically acceptable salt thereof, wherein the compound has a melting point between 210° C. and 212° C.

6. The compound of claim 1, or a pharmaceutically acceptable salt thereof, wherein R is Br.

7. The compound of claim 6, or a pharmaceutically acceptable salt thereof, wherein the compound has a melting point between 170° C. and 172° C.

8. The compound of claim 1, wherein the compound is selected from the group consisting of:

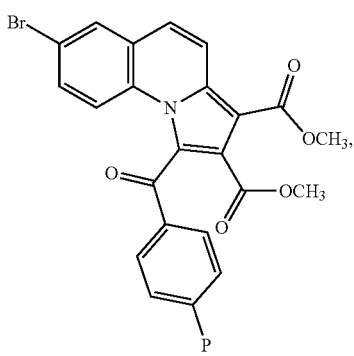

3a

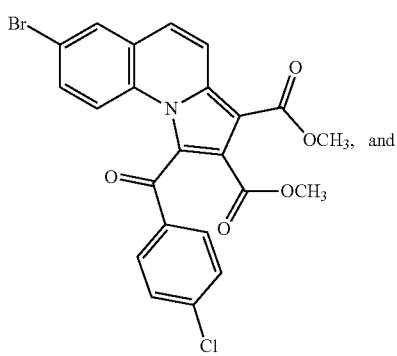

3b

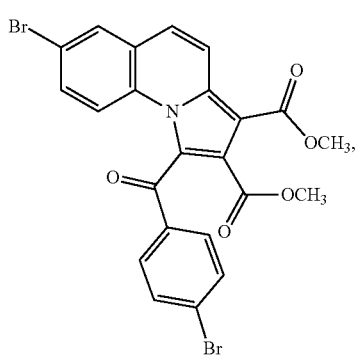

3c or a pharmaceutically acceptable salt thereof.

9. A pharmaceutical composition comprising a pharmaceutically acceptable carrier and a therapeutically effective amount of the compound of claim 1, or a pharmaceutically acceptable salt thereof.

10. A method for inhibiting inflammation in a patient, wherein the method comprises administering to the patient in need thereof therapeutically effective amount of the compound of claim 1, or a pharmaceutically acceptable salt thereof.

11. A method for treating inflammation in a patient, wherein the method comprises administering to the patient in need thereof therapeutically effective amount of the compound of claim 1, or a pharmaceutically acceptable salt thereof.

12. A compound having the formula I:

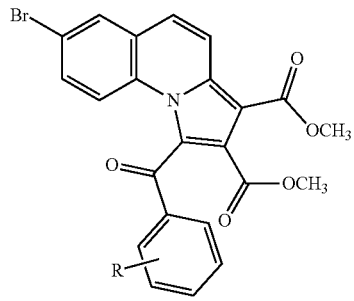

I or a pharmaceutically acceptable salt thereof,
wherein:
R is F, Cl, or Br.

13. A pharmaceutical composition comprising a pharmaceutically acceptable carrier and a therapeutically effective amount of the compound of claim 12, or a pharmaceutically acceptable salt thereof.

14. A method for treating inflammation in a patient, wherein the method comprises administering to the patient in need thereof therapeutically effective amount of the compound of claim 12, or a pharmaceutically acceptable salt thereof.

15. A compound selected from the group consisting of:

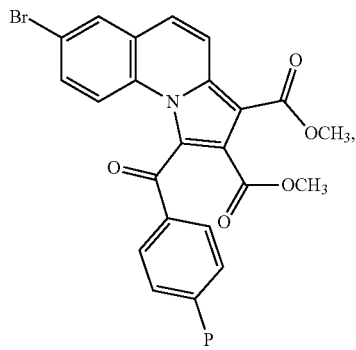

3a

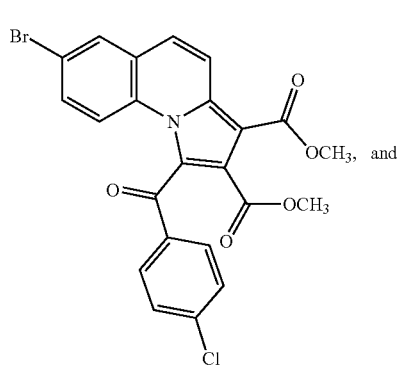

3b

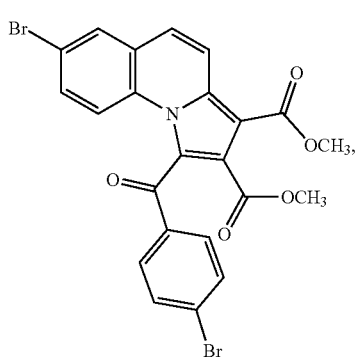

or a pharmaceutically acceptable salt thereof.

16. A pharmaceutical composition comprising a pharmaceutically acceptable carrier and a therapeutically effective amount of the compound of claim 15, or a pharmaceutically acceptable salt thereof.

17. A method for treating inflammation in a patient, wherein the method comprises administering to the patient in need thereof a therapeutically effective amount of the compound of claim 15, or a pharmaceutically acceptable salt thereof.

* * * * *